United States Patent [19]

Brunson et al.

[11] Patent Number: 5,466,251
[45] Date of Patent: Nov. 14, 1995

[54] THERAPEUTIC SLEEVE

[75] Inventors: Kevin K. Brunson, Argyle; Anthony B. Benson, Arlington, both of Tex.

[73] Assignee: Tecnol Medical Products, Inc., Fort Worth, Tex.

[21] Appl. No.: 273,094

[22] Filed: Jul. 8, 1994

[51] Int. Cl.⁶ ............................................. A61F 7/00
[52] U.S. Cl. ..................... 607/112; 607/114; 607/108
[58] Field of Search ................... 607/96, 104, 108–112, 607/114

[56] References Cited

U.S. PATENT DOCUMENTS

| | | |
|---|---|---|
| 1,549,510 | 8/1925 | Schnitzler . |
| 3,186,404 | 6/1965 | Gardner . |
| 3,595,288 | 2/1967 | Rosenfield . |
| 3,736,769 | 6/1973 | Petersen . |
| 3,856,008 | 12/1974 | Fowler et al. . |
| 3,882,873 | 5/1975 | Arango ................... 607/108 |
| 4,081,150 | 3/1978 | Tyson ..................... 607/112 |
| 4,204,543 | 5/1980 | Henderson . |
| 4,347,848 | 9/1982 | Hubbard et al. . |
| 4,372,318 | 2/1983 | Viesturs et al. ......... 607/109 |
| 4,385,950 | 5/1983 | Hubbard et al. . |
| 4,585,003 | 4/1986 | Meistrell . |
| 4,586,506 | 5/1986 | Nangle . |
| 4,628,932 | 12/1986 | Tampa . |
| 4,688,572 | 8/1987 | Hubbard et al. . |
| 4,972,832 | 11/1990 | Trapini et al. ........... 607/108 |
| 5,020,711 | 6/1991 | Kelley . |
| 5,038,779 | 8/1991 | Barry et al. . |
| 5,052,387 | 10/1991 | Natali ..................... 607/108 |
| 5,243,974 | 9/1993 | Allen . |
| 5,277,695 | 1/1994 | Johnson, Jr. et al. ... 607/104 X |

OTHER PUBLICATIONS

"Thermal Bag with Extremity Band" brochure, *Spectrum® Hydro–Med Products, Inc. Disposable Medical Products*, date unknown, one page.
"Neoprene Ice Pack Wrap" brochure, *Body Glove®*, date unknown, two pages.
"New Products" brochure, author unknown, date unknown, one page.

*Primary Examiner*—Angela D. Sykes
*Attorney, Agent, or Firm*—Baker & Botts

[57] ABSTRACT

A therapeutic elastic sleeve (12) is provided which can be affixed securely to a patient's limb. The sleeve (12) is formed from a wide sheet (18) of elastic material that is fixedly attached to the sides of an ice pack or other appropriate heat or coolant container (16). The elastic portion (18) of the sleeve can be stretched to allow the sleeve (12) to slip over the patient's limb and align the container (16) with the area to be treated. The elasticity of the sleeve (12) causes it to conform to the shape of the limb, which provides structural support to the limb and also prevents the sleeve from riding up, riding down, or telescoping on the limb.

6 Claims, 2 Drawing Sheets

THERAPEUTIC SLEEVE

TECHNICAL FIELD OF THE INVENTION

The present invention relates generally to limb therapy apparatuses, and more specifically, to an elastic sleeve that conforms to a limb to apply cold or heat therapy.

BACKGROUND OF THE INVENTION

Cold therapy is an established practice used in the medical profession to treat certain limb injuries, such as, for example, sprained or strained arm or leg muscles, or injuries to joints. Generally, these types of injuries should be chilled to slow blood flow, which reduces swelling, pain, and further damage. A typical course of cold therapy treatment is to apply ice for a specified period to the injured region of the limb. Alternatively, a pack or bag containing a chemical gel that reacts to produce cold may be applied to the injured region.

Heat therapy may be used, in other circumstances, to warm up or limber muscles by increasing blood flow. For example, athletes may apply heat with a hot water bag for a specified period to thighs or calf muscles prior to an event.

A relatively simple technique has been used in the past to chill an injured region of a limb. A plastic bag was filled with ice and placed on the injured region. However, since the bag was not secured to the limb, the patient had to be immobilized to keep the bag from falling off of the limb. Since then, medical professionals have developed a number of cold (and heat) therapy treatment products that can be affixed to a limb but still allow a patient to move around.

For example, U.S. Pat. No. 5,020,711 to Kelley, discloses a holder for reusable hot/cold packs. One or more elastic bands, which are affixed to one end of the holder, wrap around the limb to be treated, and are attached to the other end of the holder by means of a hook-and-loop fastener system (Velcro®).

U.S. Pat. No. 4,688,572 to Hubbard et al., discloses a thermal pack having two pockets connected together by a stretchable material. A waterproof bladder is inserted into each pocket. A pair of Velcro®-equipped straps are attached to the other side of one pocket. These straps extend around the limb and fasten to the brushed pile outer surface of the second pocket.

U.S. Pat. No. 4,586,506 to Nangle, discloses an elastic wrap that can be wound around a limb. A container for a hot or cold pad is attached to the elastic wrap. After the elastic wrap is wound around the limb, an attaching means (Velcro®) is used to fasten one section of the elastic wrap to a second section. A second attaching means fastens the container to a predetermined section of the wrap, which the patient aligns with the region of the limb to be treated.

U.S. Pat. No. 4,347,848 to Hubbard et al., discloses a refillable ice pack having two pairs of tie strings. The ice pack is placed on the injured region of the limb, and the tie strings are tied together to secure the ice pack to the limb.

Nevertheless, these existing hot/cold therapy devices are not always easily secured to a limb. For example, a number of these devices require the use of two hands to affix them to a limb. Consequently, it is extremely difficult for individuals to affix such devices to their own arms. Additionally, some of these existing hot/cold therapy devices tend to "ride up," "ride down," or "telescope" on the limb, which diminishes their therapeutic value. Furthermore, a number of the existing devices do not provide adequate support for an injured limb (e.g., at an injured joint), which also diminishes their therapeutic value. Moreover, a number of these devices do not hold the hot/cold pack against the limb with an evenly distributed pressure, which decreases the cooling or heating effectiveness of the device.

U.S. Pat. No. 3,736,769 to Petersen, discloses a cooling device having a thin, adjustable-length elastic band that holds the device against a patient's limb. However, because of the elastic band's thin width, the device cannot function adequately to support the limb. Furthermore, the device tends to "ride up," "ride down" or "telescopes" on the limb and does not provide an evenly distributed pressure to an injured region of the limb.

Accordingly, a need has arisen for a single cold therapy device that can be readily affixed to an injured limb, is stable and can adequately support the limb, and can evenly distribute pressure and cold to the affected region of the limb. A need also exists for a single heat therapy device that can be readily affixed to a limb.

SUMMARY OF THE INVENTION

In accordance with a preferred embodiment of the present invention, a therapeutic elastic sleeve is provided which can be affixed securely to a patient's limb. The sleeve is formed from a wide sheet of elastic material that is fixedly attached to the sides of an ice pack or other appropriate heat or coolant container. The elastic portion of the sleeve can be stretched to allow the sleeve to slip over the patient's limb and align the container with the area to be treated. The elasticity of the sleeve causes it to conform to the shape of the limb, which provides structural support to the limb and also prevents the sleeve from riding up, riding down, or telescoping.

In one aspect of the invention, a refillable ice pack is included as part of the present sleeve, which is of the general type disclosed in U.S. Pat. No. 4,347,848 to Hubbard et al. The ice pack takes the form of a generally rectangular envelope having two sides, an open end and a closed end. The wide sheet of elastic material is fixedly attached to each of the two sides. The envelope may be formed of a multiple ply material including, for example, at least an inner layer of waterproof material, an intermediate layer of absorbent material, and an outer layer of absorbent material. The combination of the intermediate and outer layers provides a wicking effect, which permits evaporation of water condensing at the interface of the inner layer and the intermediate layer so that the outside of the ice pack does not become wet and unsuitable for reuse because of condensation.

In a second aspect of the invention, a second ice pack or appropriate coolant container may be included as part of the present sleeve. Consequently, the second ice pack may be aligned with a second area of the limb to be treated, or aligned with the same injured region but from the opposite side of the limb.

In a third aspect of the invention, the present sleeve has two openings through which the limb is passed. One opening may be formed wider than the other opening so that the shape of the sleeve can approximate the taper of the limb to better conform to the limb.

In a fourth aspect of the invention, an upper portion of the elastic material may be formed from a substantially thicker and/or stronger elastic material than the lower portion so that the upper portion may be grasped firmly to facilitate pulling the sleeve onto the limb without tearing the elastic material or the sleeve.

In a fifth aspect of the invention, a material having a relatively high coefficient of friction may be bonded or otherwise applied to an inner surface portion of the sleeve to prevent the sleeve from riding up, riding down or telescoping on a limb.

In yet a sixth aspect of the invention, a heat pack or similar container for heated material may be substituted for the present ice pack to provide heat therapy to a person's limb.

An important technical advantage of the invention is that the present sleeve can be slipped onto a person's limb using one hand.

Another important technical advantage of the invention is that the present sleeve can maintain a proper and stable fit around a person's limb.

Another important technical advantage of the invention is that the present sleeve can provide adequate structural support for an injured limb.

Another important technical advantage of the invention is that the present sleeve can hold the ice pack or other coolant container against an injured area of a limb with evenly distributed pressure for more effective treatment.

Yet another important advantage of the present invention is that all of the above-described advantages can be provided with a single therapeutic device.

DETAILED DESCRIPTION OF THE INVENTION

The preferred embodiment of the present invention and its advantages are best understood by referring to FIGS. 1–5 of the drawings, like numerals being used for like and corresponding parts of the various drawings.

Figure 1:
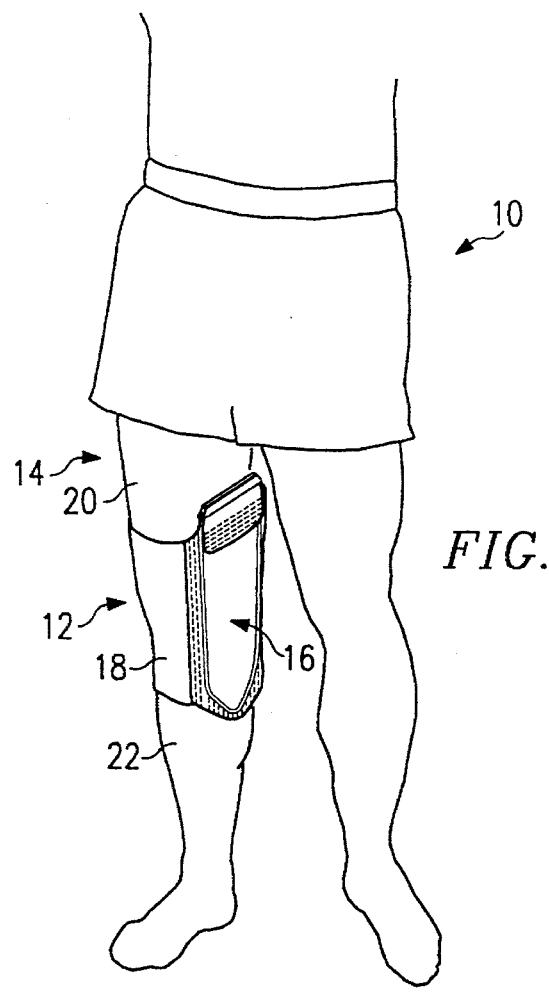
FIG. 1 is a perspective view of a preferred embodiment of the present therapeutic sleeve in use on the leg of a patient.

FIG. 1 shows a patient 10 wearing a therapeutic sleeve 12 structured and functioning in accordance with a preferred embodiment of the present invention. For illustrative purposes only, therapeutic sleeve 12 is shown positioned specifically to chill the knee region of leg 14. Sleeve 12 may include a container 16 for holding a coolant material (not explicitly shown). In an aspect of the invention, container 16 may comprise an ice pack for holding ice, or a chemical gel that functions to generate cold. In another aspect of the invention, container 16 may comprise a heat pack or other appropriate container for holding a heated material (not explicitly shown). A sheet 18 may be constructed of an elastic material that can be fixedly (not removably) attached to each side of container 16 to form, in combination with container 16, therapeutic sleeve 12. In a preferred embodiment, sheet 18 may be constructed, for example, of a "Stretch Bonded Laminate" fabric manufactured by Kimberly-Clark. However, the scope of the present invention is not intended to be limited to a particular type of material for sheet 18. Any appropriate material may be substituted for sheet 18, as long as it performs the function of stretching and recovering in shape to allow sleeve 12 to be donned and conform substantially to the shape of a limb.

Because sheet 18 is constructed of an elastic material, therapeutic sleeve 12 conforms substantially to the shape of the patient's limb (e.g., leg 14) and maintains a proper and stable fit around the affected area of the limb. Furthermore, the elastic function of therapeutic sleeve 12 provides substantial structural support to stabilize the affected limb and also hold container 16 against the limb with a substantially evenly distributed pressure adjacent the limb. Moreover, the relatively large width of sheet 18 functions to stabilize the movement of sleeve 12 with respect to the limb so that the sleeve does not "ride up," "ride down," or "telescope" on the limb. Notably, the patient may slip sleeve 12 on over an injured limb with the use of only one hand. This feature is particularly advantageous if a patient lacks assistance but needs to place the therapeutic sleeve on an arm, or the patient only has the use of one hand.

In a second aspect of the invention, sheet 18 may be constructed to form a tapered sleeve. For example, referring to FIG. 2, which is an isometric view of the therapeutic sleeve illustrated by FIG. 1, sheet 18 may be formed with an upper edge 17 and a lower edge 19. Upper edge 17 may be significantly longer than lower edge 19. Consequently, sleeve 12 would be formed so that one opening is wider than the other. Specifically, in this aspect of the invention, upper opening 21 of sleeve 12 is wider than lower opening 23. Therefore, by exerting virtually identical pressure around both the upper (wider) and lower (narrower) portions of tapered sleeve 12, the present sleeve can prevent "riding up," "riding down," or "telescoping" by securely and comfortably fitting around a tapered portion of a limb, such as a forearm or thigh. In any event, even if the present therapeutic sleeve is formed with a taper, such a conformable sleeve may be used just as effectively around a relatively untapered region of a limb, such as, for example, around an upper arm.

As shown in FIG. 1, sleeve 12 fits securely around, and conforms substantially to, the shape of leg 14, which tapers inwardly from thigh portion 20 to calf portion 22. Consequently, in accordance with the teachings of the invention, a tapered therapeutic sleeve 12 will neither hinder circulation in thigh portion 20 by fitting too tightly, nor will it fit too loosely around calf portion 22. Also, the present tapered sleeve provides an added advantage. Since one opening of the sleeve is wider than the other, a patient may slip the sleeve onto a limb relatively easily by inserting the limb through the wider opening first, in a manner similar to that used to don a pants leg or shirt sleeve.

In another aspect of the invention, an upper portion of sheet 18 proximate edge 17 may be formed from a substantially thicker and/or stronger elastic material than the lower portion of sheet 18, so that the upper portion of sheet 18 may be grasped firmly to facilitate pulling the sleeve onto the limb without tearing the elastic material or the sleeve.

Figure 2:
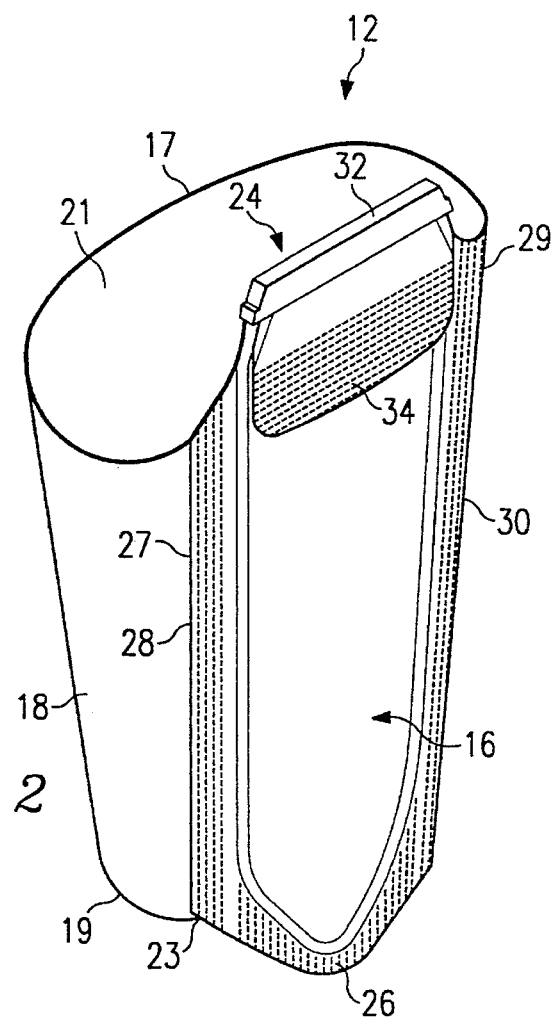
FIG. 2 is an isometric view of the therapeutic sleeve of FIG. 1.

Although the embodiment illustrated by FIGS. 1 and 2 is shown with a taper, this feature is not intended to limit the invention in this regard. For example, upper opening 21 and lower opening 23 may have substantially equal diameters (unstretched). Albeit, in an aspect related to an untapered embodiment of the present invention (which could apply equally well to the tapered version in FIGS. 1 and 2), a material having a relatively high coefficient of friction may be applied to all or a portion of the inner surface of sheet 18 to ensure the stability and placement of the cold/heat container with respect to the limb. For example, an adhesive material may be applied or attached to the inner surface of sheet 18 (facing the surface of the limb). The resulting adhesive region may then be activated to adhere, or at least not slip, with respect to the limb, in response to a predetermined increase in temperature, pressure, and/or wetness. Consequently, by substituting a material having a selectively or fixed, high coefficient of friction for all or a portion of the inner surface of sheet 18, an untapered version of the present sleeve can prevent "riding up," "riding down," or "telescoping" on a limb under conditions that could normally cause such an effect.

Referring again to FIG. 2, in another aspect of the invention, container 16 may comprise an ice pack including a generally rectangular envelope having an open end 24, a closed end 26, and opposing sides 28 and 30. Generally, the envelope may be formed of a multiple ply material containing, for example, an inner layer of waterproof material, an intermediate layer of a first absorbent material, and an outer layer of a second absorbent material. The combination of the intermediate and outer layers of material provides a wicking effect, which permits evaporation of water condensing at the interface of the inner layer and the intermediate layer so that the outside of the ice pack does not become wet and unsuitable for reuse because of condensation. In this aspect of the invention, ice pack 16 may be generally of the type described in U.S. Pat. No. 4,347,848 to Hubbard et al., which is incorporated herein by reference for all purposes. However, the pertinent details of ice pack 16 are described below with respect to FIGS. 4 and 5.

Figure 4:
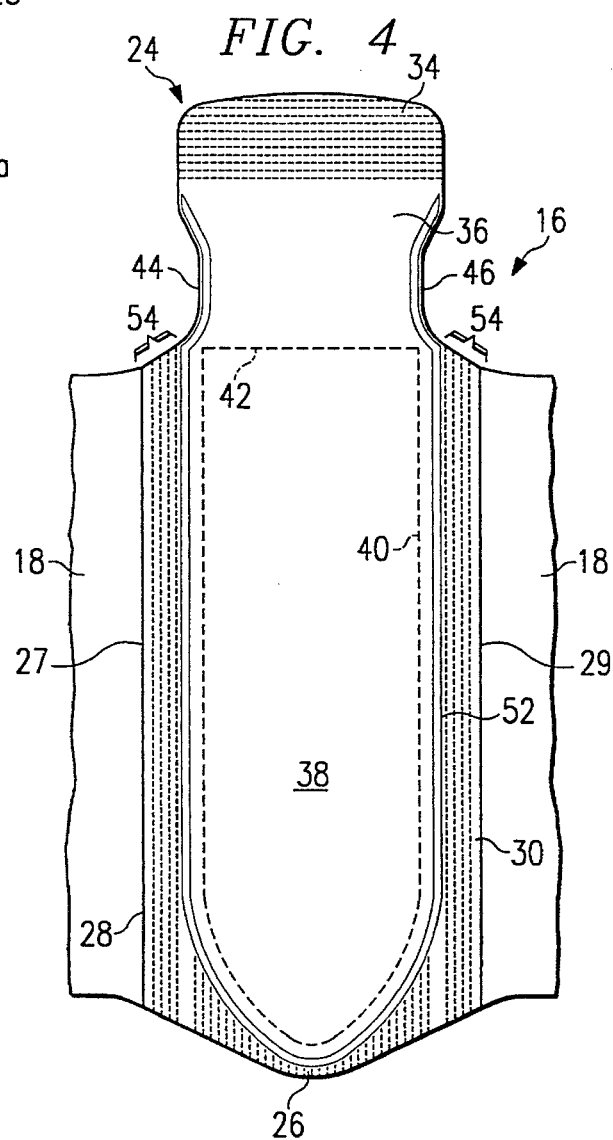
FIG. 4 is a side view showing additional details of an ice pack that may be used with the therapeutic sleeves embodied in FIGS. 2 and 3.

Ice pack 16 may also include a closure member 32 which is employed selectively to seal (or open) open end 24 of the envelope after the ice pack is filled with ice. Closure member 32 may be generally of the type described in U.S. Pat. No. 4,347,848 to Hubbard et al. Also, closure member 32 may be curved slightly to conform generally to the shape of a limb. However, any appropriate closure may be substituted for closure member 32, as long as it performs the function of selectively sealing the open end of the ice pack. Referring to FIGS. 2 and 4 (to be described in detail below), closure member 32 may be grasped to facilitate pulling the present sleeve onto the limb.

The edges 27 and 29 of sheet 18 may be fixedly attached or bonded to respective sides 28 and 30 of ice pack 16 employing certain attachment or bonding technologies such as, for example, adhesive bonding, sonic welding, stitching, or heat and pressure sealing. An advantage of fixedly attaching elastic sheet 18 to container 16 is that the manually adjustable attachments used in existing devices may be eliminated. As shown in FIG. 2, sheet 18 may be tapered inwardly from upper edge 17 to lower edge 19. Therefore, the length of upper edge 17 is greater than the length of lower edge 19. Alternatively, in a different aspect of the invention, upper and lower edges 17 and 19 may be constructed with substantially equal lengths, thus forming in combination with container 16, a substantially tubular-shaped structure for sleeve 12.

Figure 3:
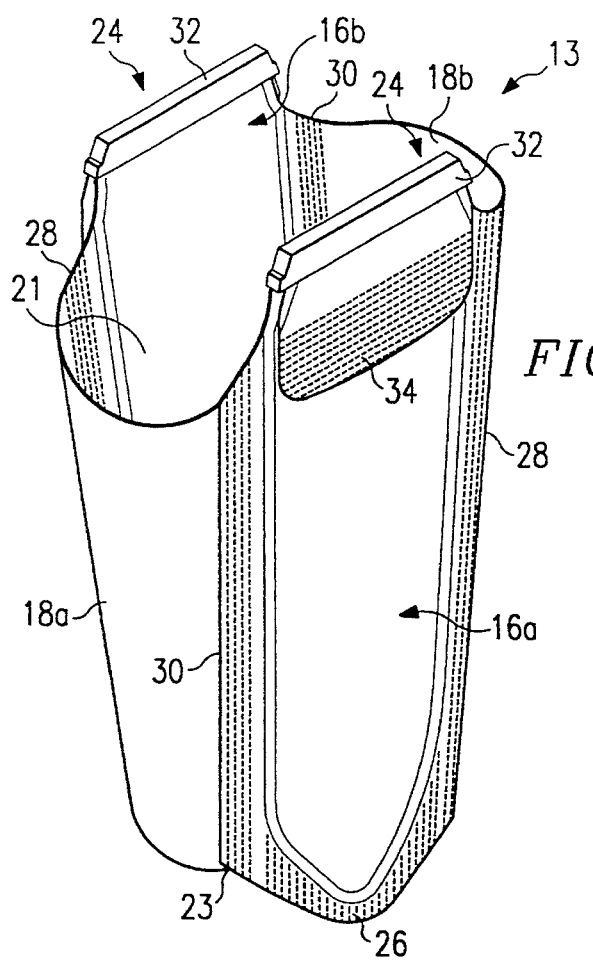
FIG. 3 is a second embodiment of the therapeutic sleeve illustrated by FIG. 2.

FIG. 3 is an isometric view of a second embodiment of the therapeutic sleeve illustrated by FIG. 2. Sleeve 13 may include two ice packs or containers 16a and 16b fastened to two elastic sheets 18a and 18b. Elastic sheets 18a and 18b may be tapered inwardly similar to the taper of sleeve 12 described with respect to FIG. 2. Using two ice packs 16a and 16b, sleeve 13 may function to chill the opposite sides of a limb. Alternatively, if such dual treatment is unnecessary, a patient may fill only one of the ice packs with ice and forgo use of the second pack without sacrificing any of the above-described advantages of the invention. Furthermore, although sleeve 13 is depicted, for illustrative purposes only, with two ice packs or containers 16, it is within the scope of the invention to use three or more ice packs or containers 16 to form sleeve 13, being limited only by the size of the sleeve.

FIG. 4 is a side view showing additional details of an ice pack that may be used with the therapeutic sleeves embodied in FIGS. 2 and 3. Two panels 36 (one of which is not explicitly shown) are sealed or otherwise bonded together along sides 28 and 30 and closed end 26, to form a generally rectangular envelope and internal pocket. A waterproof bag 38 (indicated by the dotted lines), which may be constructed of polyethylene or other appropriate waterproof material, is formed from sealing or bonding three sides of the pocket. Bag 38 may be sealed by sonic welding or other any other appropriate technique along sides 28, 30 and closed end 26. Bag 38 may include a throat 42 that opens outwardly of the open end of the ice pack. As a design feature, throat 42 may have diverging walls 44 and 46 to facilitate the filling of ice pack 16 with ice, although such diverging walls are not critical aspects of the invention.

Referring still to FIG. 4, the edges 27 and 29 of sheet 18 may be fixedly attached to respective sides 28 and 30 of ice pack 16 along seams 54, by employing certain attachment or bonding technologies such as, for example, adhesive bonding, sonic welding, stitching, or heat and pressure sealing.

Figure 5:
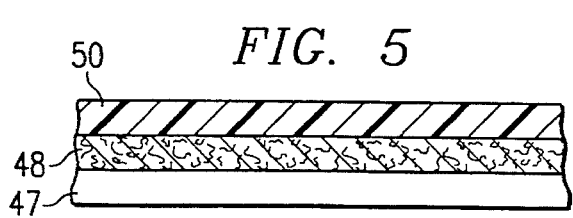
FIG. 5 is a cross-sectional view of the material from which the ice pack embodied in FIG. 4 may be constructed.

FIG. 5 is a cross-sectional view of the materials from which the ice pack embodied in FIG. 4 may be constructed. Innermost layer 47, which is used to form waterproof bag 38, may be constructed of a sheet of polyethylene or other appropriate waterproof material. Innermost layer 47 may be bonded to an intermediate layer 48 constructed preferably from a first absorbent material, such as, for example, a hydrophilic nonwoven or woven web material. Alternatively, intermediate layer 48 may be constructed from any appropriate material that performs the function of wicking condensation away from the outer surface of the innermost layer to the outer layer 50. Outer layer 50 may be constructed preferably from a second absorbent material, such as, for example, a hydroentangled, polyester nonwoven material. In one aspect of the invention, the intermediate and outer layers may be constructed from the same material. However, outer layer 50 is not intended to be limited to a particular type of material and may be constructed from any appropriate material that performs the function of evaporating water received from the intermediate layer at a rate sufficient to prevent the outside of ice pack 16 from becoming wet and unsuitable for reuse because of condensation.

Although the present invention and its advantages have been described in detail, it should be understood that various changes, substitutions and alterations can be made therein without departing from the spirit and scope of the invention as defined by the appended claims.

What is claimed is:

1. A stretchable therapeutic sleeve, comprising:

a thin sheet of relatively wide elastic material, said sheet including a first side, a second side opposing said first side, a top edge and a bottom edge; and a heat or cold pack container, said container including a third side and a fourth side opposing said third side, said first side fixedly joined to said third side, and said second side fixedly joined to said fourth side, wherein a thickness of said sheet proximate said top edge is greater than a thickness of said sheet proximate said bottom edge so as to allow an upper portion of said sheet to be grasped firmly to facilitate pulling the sleeve onto a user's limb.

2. A stretchable therapeutic sleeve, comprising:

a first thin sheet of relatively wide elastic material, said first sheet including a first side, a second side opposing said first side, a first top edge and a first bottom edge;

at least a second thin sheet of relatively wide elastic material, said at least second sheet including a third side, a fourth side opposing said third side, a second top edge and a second bottom edge;

a first heat or cold pack container, said first container including a fifth side and a sixth side opposing said fifth side; and at least a second heat or cold pack container, said at least second container including a seventh side and an eighth side opposing said seventh side, said first side fixedly joined to said sixth side and said second side fixedly joined to said seventh side, said third side fixedly joined to said eighth side and said fourth side fixedly joined to said fifth side, the length of said first top edge being greater than the length of said first bottom edge, and the length of said second top edge being greater than the length of said second bottom edge, said sleeve thereby defining an inwardly tapered, substantially tubular surface to conform substantially to the shape of a user's limb.

3. The stretchable therapeutic sleeve according to claim 2, wherein said first container and said second container each comprise an ice pack.

4. A method for constructing a therapeutic sleeve, comprising the steps of:

positioning in overlapping relation first and second strips of at least a three ply material of the type having at least an inner layer of waterproof material, an intermediate layer of a first absorbent material, and an outer layer of a second absorbent material;

sealing said first and second strips together along a first side and a second side thereof and along one end thereof to form an envelope;

sealing said first and second strips together in an interior of said envelope to form a bag member being open at the open end of said envelope and closed on all other sides;

positioning in overlapping relation said first side of said envelope with a third side of a thin sheet of relatively wide elastic material, and said second side of said envelope with a fourth side of said thin sheet of relatively wide elastic material, said third side opposite said fourth side; and sealing said first side and third side together and said second side and fourth side together to form said sleeve.

5. The method according to claim 4, wherein the sealing steps further comprise ultrasonically sealing.

6. A method of constructing a therapeutic sleeve, comprising the steps of:

positioning in overlapping relation a first side of a thin sheet of relatively wide elastic material with a second side of a container, and a third side of said thin sheet of relatively wide elastic material with a fourth side of said container, said container being adapted to contain hot or cold material; and sealing said first side and said second side together, and said third side and said fourth side together to form said sleeve.

* * * * *